(12) United States Patent
Ge et al.

(10) Patent No.: US 8,119,092 B2
(45) Date of Patent: Feb. 21, 2012

(54) PEGYLATION AND HYDROXYLATION OF TRIMETALLIC NITRIDE ENDOHEDRAL METALLOFULLERENES

(75) Inventors: Zhongxin Ge, Blacksburg, VA (US); Harry C. Dorn, Blacksburg, VA (US); J. Paige Phillips, Hattiesburg, MS (US)

(73) Assignee: Luna Innovations Incorporated, Roanoke, VA (US)

( * ) Notice: Subject to any disclaimer, the term of this patent is extended or adjusted under 35 U.S.C. 154(b) by 1101 days.

(21) Appl. No.: 10/594,432

(22) PCT Filed: Mar. 25, 2005
(Under 37 CFR 1.47)

(86) PCT No.: PCT/US2005/010219
§ 371 (c)(1),
(2), (4) Date: Nov. 16, 2007

(87) PCT Pub. No.: WO2005/097807
PCT Pub. Date: Oct. 20, 2005

(65) Prior Publication Data
US 2008/0166285 A1 Jul. 10, 2008

Related U.S. Application Data

(60) Provisional application No. 60/556,432, filed on Mar. 26, 2004.

(51) Int. Cl.
*C01B 31/02* (2006.01)
(52) U.S. Cl. ............... 423/445 B; 977/736; 977/737; 977/738

(58) Field of Classification Search ............. 423/445 B; 977/734–741, 846–847
See application file for complete search history.

(56) References Cited

U.S. PATENT DOCUMENTS

| | | | |
|---|---|---|---|
| 5,453,413 A | 9/1995 | Eklund | |
| 6,063,243 A | 5/2000 | Zettl et al. | |
| 6,303,760 B1 | 10/2001 | Dorn et al. | |
| 6,355,225 B1 * | 3/2002 | Alford et al. | 424/9.3 |
| 6,471,942 B1 * | 10/2002 | Miller et al. | 424/9.1 |
| 6,538,153 B1 * | 3/2003 | Hirsch et al. | 560/82 |
| 2001/0050219 A1 | 12/2001 | Anazawa et al. | |
| 2002/0061638 A1 | 5/2002 | Takikawa et al. | |
| 2003/0015414 A1 | 1/2003 | Kajiura et al. | |
| 2003/0031917 A1 | 2/2003 | Katori et al. | |
| 2003/0065206 A1 * | 4/2003 | Bolskar et al. | 558/87 |
| 2004/0054151 A1 | 3/2004 | Dorn et al. | |
| 2005/0067349 A1 | 3/2005 | Crespi et al. | |

OTHER PUBLICATIONS

Tabata, et al., Biological functions of fullerene, Pure Appl. Chem. 1999; 71(11): 2047-2053.*
Fatouros, et al., In Vitro and in Vivo Imaging Studies of a New Endohedral Metallofullerene Nanoparticle, Radiology 2006; 240(3): 756-764.*

(Continued)

*Primary Examiner* — Daniel C. McCracken
(74) *Attorney, Agent, or Firm* — Albrecht Tousi & Farnum PLLC; Susan M. Dadio

(57) ABSTRACT

A pegylated and hydroxlated trimetallic nitride endohedral metallofullerene is provided comprising a plurality of hydroxyl groups and one or more polyethylene glycol (PEG) moieties covalently bonded to a fullerene encapsulating a trimetallic nitride. Methods of pegylation and hydroxylation of trimetallic nitride endohedral metallofullerene and methods of using pegylated and hydroxlated trimetallic nitride endohedral metallofullerene are described.

10 Claims, 3 Drawing Sheets

OTHER PUBLICATIONS

Iezzi, Erick B. et al., "A Symmetric Derivative of the Trimetallic Nitride Endohedral Metallofullerene, $Sc_3N@C_{80}$," J.Am.Chem.Soc., 2002, pp. 524-525, vol. 124, No. 4, American Chemical Society.

Kratschmer, W. et al., "Solid $C_{60}$: a new form of carbon," Nature, Sep. 27, 1990, pp. 354-358, vol. 347, Nature Publishing Group.

Olmstead, Marilyn M. et al., "Isolation and Crystallographic Characterization of $ErSc_2N@C_{80}$: an Endohedral Fullerene Which Crystallizes with Remarkable Internal Order," J.SM.VHRM.Soc., 2000, pp. 12220-12226, vol. 122, No. 49, AmericanChemical Society.

Stone, A.J. et al., "Theoretical Studies of Icosahedral $C_{60}$ and Some Related Species," Chem. Physics Ltrs., Aug. 8, 1986, pp. 501-503, vol. 128, No. 5,6, Elsevier Science Publishers B.V.

Trulove, "Filled buckyballs—diamonds from soot," article from website http://www.research.vt.edu/resmag/2002winter/buckyballs.html, Mar. 9, 2002, available at www.archive.org. (entire document).

Nagase et al., Chapter 9: Endohedral metallofullerenes: theory, electrochemistry, and chemical reactions, of Fullerenes: Chemistry, Physics and Technology (Kadish and Ruoff, eds.), 2000, John Wiley and Sons, pp. 395-429.

Zhang et al., "The tribological behaviors of ordered system ultrathin films," *Science*, 2003, vol. 254, pp. 959-964, Elsevier Science, B.V., London, England.

Journet et al., "Large-scale production of single-walled carbon nanotubes by the electric-arc technique," *Nature*, 1997, vol. 388, pp. 756-758, American Association for the Advancement of Science, Washington, D.C.

Saito et al., "Single-Layered Carbon Nanotubes Synthesized by Catalytic Assistance of Rare-Earths in a Carbon Arc," *J. Phys. Chem.*, 1995, vol. 99, pp. 16076-16079, American Chemical Society, Washington, D.C.

Wilson et al., "Advanced materials: fluorous fullerenes and nanotubes," *Tetrahedron*, 2002, vol. 58, pp. 4041-4047, Elsevier Science Ltd.

* cited by examiner

PEGYLATION AND HYDROXYLATION OF TRIMETALLIC NITRIDE ENDOHEDRAL METALLOFULLERENES

BACKGROUND OF THE INVENTION

This application is related to the field of carbonaceous nanomaterials, for example, functionalized fullerenes.

Methods of making endohedral metallofullerenes have been previously described, for example in U.S. Pat. No. 6,303,760. "Endohedral metallofullerenes" refers to the encapsulation of atoms inside a fullerene cage network. A family of trimetallic nitride endohedral metallofullerenes can be represented generally as $A_{3-n}X_nN@C_m$; where A and X are metal atoms, n=0–3, and m can take on even values between about 60 and about 200. All elements to the right of an @ symbol are part of the fullerene cage network, while all elements listed to the left are contained within the fullerene cage network. As an example, $Sc_3N@C_{80}$ indicates that a $Sc_3N$ trimetallic nitride is situated within a $C_{80}$ fullerene cage.

Trimetallic nitride endohedral metallofullerenes can have properties that find utility in conductors, semiconductor, superconductors, or materials with tunable electronic properties such as optical limiters, nonlinear optical devices, ferroelectrics. For example, trimetallic nitride endohedral metallofullerenes having encapsulated radioactive metals, such as Ho, may be used for medical applications such as radioactive tracers. These tracers may serve as fluorescent or optical tags.

SUMMARY OF THE INVENTION

Despite the foregoing, there is a need in the art for modified endohedral metallofullerenes having desirable properties, for example functionalized endohedral metallofullerenes having enhanced water solubility while minimizing aggregation.

A pegylated and hydroxlated trimetallic nitride endohedral metallofullerene is provided comprising a plurality of hydroxyl groups and one or more polyethylene glycol (PEG) moieties covalently bonded to a fullerene encapsulating a trimetallic nitride. Preferably, the polyethylene glycol is covalently bonded to the fullerene through a malonyl moiety. For example, the one or more polyethylene glycol moiety can be covalently bonded to the fullerene through an ethyl malonyl moiety. In another example, wherein one or more pairs of polyethylene glycol moieties can be covalently bonded to the fullerene through a malonyl moiety.

Preferably, the polyethylene glycol moiety has a molecular weight chosen from about 350, 550, 750, 2000 and 5000. Alternatively, the PEG can preferably have about 2 to 400, or more polyethylene units, for example the PEG can preferably have about 4, 7, 9, 11, 16, 20, 40, 100, 200, 400, or more units.

Preferably the PEG is an alkoxy-PEG, for example the polyethylene glycol moiety can be methoxypolyethylene glycol. Alternatively, the PEG can have a functional derivative at a terminus.

An endohedral metallofullerene of the formula $A_{3-n}X_nN@C_m(-R(-[-O-CH_2CH_2-]_k-Q)_j)_i(-OH)_h$; where A and X are metal atoms, n=0–3; m is an even number between about 60 and about 200; 1<h<m-2; i≧1; j=1 or 2 and k>1 is provided. In a preferred example, j=1 and R is an ethyl malonyl group. Q can preferably be a methoxy group. In an alternative preferred embodiment, j=2 and R is a malonyl group. In preferred embodiments, k is about 7, 11, 16 or greater, for example 40 or greater. In preferred examples, A and/or X are rare earth elements and/or a group IIIB element. In preferred examples, A and/or X are chosen from among the group consisting of Scandium, Yttrium, Lanthanum, Gadolinium, Holmium, Erbium, Thulium, and Ytterbium.

A method of pegylation and hydroxylation of trimetallic nitride endohedral metallofullerene comprising, reacting a malonyl-polyethylene glycol with a trimetallic nitride endohedral metallofullerene to form a pegylated trimetallic nitride endohedral metallofullerene; reacting the pegylated trimetallic nitride endohedral metallofullerene with NaOH and TBAH in an organic solvent; and, transferring the reacted pegylated trimetallic nitride endohedral metallofullerene into $H_2O$ in the presence of $O_2$ and $H_2O_2$. In a preferred example, the malonyl-polyethylene glycol is ethyl malonyl methoxypolyethylene glycol. In another example, the malonyl-polyethylene glycol is malonyl dimethoxypolyethylene glycol.

DETAILED DESCRIPTION OF THE PREFERRED EMBODIMENTS OF THE INVENTION

A preferred family of trimetallic nitride endohedral metallofullerenes can be represented generally as $A_{3-n}X_nN@C_m$; where A and X are metal atoms, n=0–3, and m can take on even values between about 60 and about 200. To form a trimetallic endohedral metallofullerene having a cage size between about 68 carbon atoms and about 80 carbon atoms, the metal atoms are preferably trivalent and have an ionic radius below about 0.095 nm. When m is about 68, the metal atoms preferably have an ionic radius below about 0.090 nm for the $A_3N$ endohedral species. For the $AX_2N$ and $A_2XN$ endohedral species, the larger atomic radius of 0.095 nm for A can be accommodated. As the size of the cage increases, the ionic radius for the metal may increase. Further, A and X may be a rare earth element, a group IIIB element, or the like. Preferably, A or X may be Scandium, Yttrium, Lanthanum, Gadolinium, Holmium, Erbium, Thulium, and Ytterbium.

Trimetallic nitride endohedral metallofullerenes are relatively hydrophobic. One approach to increasing the water solubility of trimetallic nitride endohedral metallofullerenes is to covalently modify the surface of the fullerene, for example by attaching hydrophilic groups such as by hydroxylating the exterior of the fullerene cage. However, hydroxylated trimetallic endohedral metallofullerenes can still exhibit aggregation, which may be undesirable. Water solubility of trimetallic nitride endohedral metallofullerenes can be enhanced with minimal aggregation by covalently bonding polyethylene glycol (PEG) to trimetallic endohedral metallofullerenes in combination with hydroxylation.

The combination of pegylation and hydroxylation of trimetallic nitride endohedral metallofullerenes can provide substantially greater dispersion and reduced aggregation in aqueous solutions relative to a single treatment. Without wishing to be bound by theory, it is believed that this results from a combination of increases in solubility due to the presence of hydrophilic groups and the greater colloidal stabilization provided by the steric repulsion of the relatively large PEG groups.

Covalently attaching PEG to a molecule can be referred to as pegylation. PEG is a biocompatible polymeric molecule of general formula H—[—O—CH$_2$CH$_2$—]$_k$—OH that is widely used for a variety of applications. PEG is widely available in compositions having a wide range of molecular weights, i.e. about 350, 550, 750, 2000, 5000 and higher and is available or can be made with a wide range of derivatives at one or both termini. To list just two examples, O-methyl-heptaethylene glycol having a molecular weight of about 340 and O-methyl-undecaethylene glycol having a molecular weight of about 516 are both available from Sigma-Aldrich. PEG of any molecular weight, preferably derivatized at one end, for example in a form such as HO-PEG-O-methyl, can be used in making pegylated and hydroxylated trimetallic nitride endohedral metallofullerenes.

Figure 1:
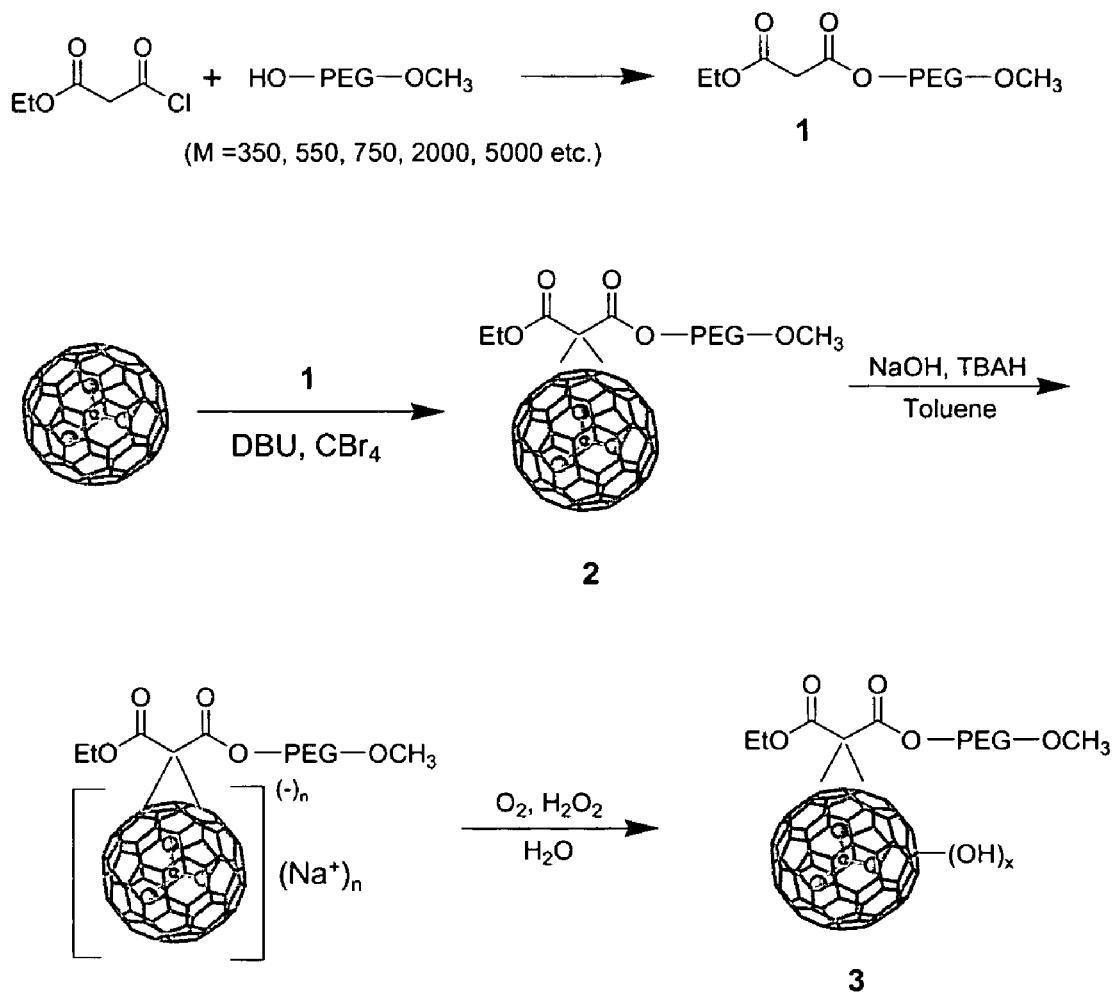
FIG. 1 illustrates a method of combined pegylation and hydroxylation of trimetallic nitride endohedral metallofullerenes.
Figure 2:
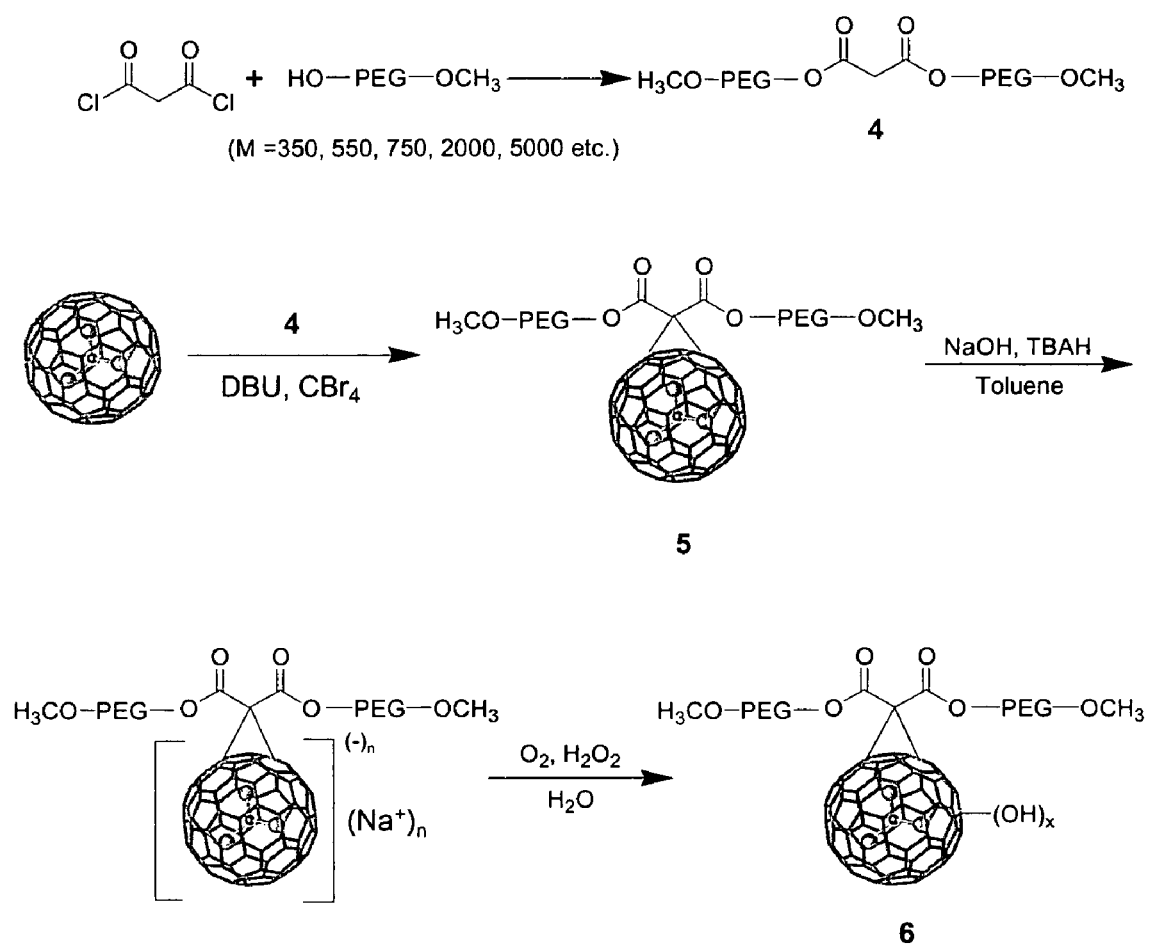
FIG. 2 illustrates an alternative method of combined pegylation and hydroxylation of trimetallic nitride endohedral metallofullerenes.

Referring to FIG. 1, an exemplary method of pegylation and hydroxylation of trimetallic nitride endohedral metallofullerenes is illustrated. In a first step, ethyl malonyl methoxy-polyethylene glycol 1 can be obtained by reacting a methoxy-polyethylene glycol with ethyl malonyl chloride. For example, about 0.01 mol of ethyl malonyl chloride (ethyl 3-chloro-3-oxopropanoate) can be reacted with about 0.01 mol methoxy polyethelene glycol in about 200 ml of dichloro methane with about 0.01 mol pyridine at room temperature for about 4 hours, after which the malonyl methoxy-polyethylene glycol is recovered by separation on a silica gel column. In a second step, trimetallic nitride endohedral metallofullerene can be pegylated by reacting the trimetallic nitride endohedral metallofullerene with malonyl-PEG (for example o-(ethylmalonyl)-o'-methyl-PEG) DBU and CBr$_4$. For example, 1 equivalent of A$_{3-n}$X$_n$N@C$_m$ and 1.5 equivalents of CBr$_4$ can be dissolved in about 80 ml of toluene with sonication. To this mixture, 1.5 equivalents of ethyl malonyl methoxy-polyethylene glycol and 3 equivalents of 1,8-diazobicyclo[5.4.0]undec-7-ene (DBU) can be added. The reaction can be stirred for about 20 hours under nitrogen at room temperature. Pegylated trimetallic nitride endohedral metallofullerene product 2 can be separated using a silica gel column. The pegylated trimetallic nitride endohedral metallofullerene can be hydroxylated by treating with NaOH and tetrabutyl ammonium hydroxide (TBAH) in toluene, followed by addition of hydrogen peroxide and water. For example, about 4 mg of pegylated trimetallic nitride endohedral metallofullerene can be dissolved in about 40 ml of toluene. About 5 drops of NaOH and about 3 drops TBAH can be added. The mixture can be allowed to react for about 2 hours before addition of about 20 ml of distilled water and about 5 drops of hydrogen peroxide. This mixture can be stirred overnight and the reaction product, hydroxylated pegylated trimetallic nitride endohedral metallofullerene 3 can be separated using a G-25 Sephadex column. Referring to FIG. 2, another example is illustrated in which malonyl dichloride is utilized so that two PEG moieties are added for each pegylation reaction first making malonyl di-(methoxy-polyethylene glycol) 4 which is reacted with trimetallic nitride endohedral metallofullerene to produce di pegylated trimetallic nitride endohedral metallofullerene product 5 which is hydroxylated to form the product, hydroxylated di-pegylated trimetallic nitride endohedral metallofullerene 6.

Methods for making the family of A$_{3-n}$X$_n$N@C$_m$ metallofullerenes include using a Kratschmer-Huffman generator. This type of generator typically has a reaction chamber that can be easily evacuated and charged with a controlled pressure of an inert gas such as helium. The generator holds two electrodes within the reaction chamber and is able to apply a potential across the electrodes to produce an arc discharge. Methods can include mounting a graphite rod, or other source of carbon, that has been filled with a mixture of a metal oxide and graphite in the reaction chamber. The metal oxide contains the metal to be encapsulated in the fullerene cage. The graphite rods are typically cored and filled with a mixture of metal oxide and graphite. The metal oxide may be the oxide of a trivalent metal. Preferably the metal oxide is the oxide of a rare earth metal or a group IIIB metal. Metal oxides may include, but are not limited to, Er$_2$O$_3$, Ho$_2$O$_3$, Y$_2$O$_3$, La$_2$O$_3$, Gd$_2$O$_3$, Tm$_2$O$_3$, or Yb$_2$O$_3$. The mixture of metal oxide and graphite may be from about 1% to about 5% metal oxide to graphite by weight. Typically, a 3% metal oxide to graphite loading will produce the desired trimetallic nitride endohedral metallofullerene.

When the encapsulation of more than one type of metal in the fullerene cage is desired, the cored graphite rod is filled with a mixture of metal oxides and graphite. The mixture of metal oxides preferably corresponds to the desired metals and graphite. The metal oxides may be combination of trivalent metals in the form of oxides. Preferably, the metals are rare earth metal oxides or group IIIB metal oxides. The metal oxides may include, but are not limited to, E$_2$O$_3$, Ho$_2$O$_3$, Y$_2$O$_3$, La$_2$O$_3$, Gd$_2$O$_3$, Tm$_2$O$_3$, or Yb$_2$O$_3$. The relative portion of each metal oxide may be from a 1% to about 5% metal oxide to graphite. Small amounts of cobalt oxide may be added to the mixture to enhance the formation of fullerenes. The addition of about 1 mg to about 425 mg of cobalt oxide may be added to the mixture. Typically, the addition of between about 75 mg and about 225 mg of cobalt oxide to the mixture will enhance the formation of the endohedral fullerenes.

Once the mixture is loaded into the cored graphite rod, the rod is place in the generator and the reaction chamber is evacuated. Helium can be introduced into the reaction chamber at about 300 torr along with a small amount of nitrogen gas, about 1 to about 3 torr. A dynamic atmosphere ranging from about 300 ml/min to 1250 ml/min helium and about 20 ml/min to about 300 ml/min nitrogen gas may also be utilized. The ratio of helium to nitrogen is not critical. The trimetallic nitride endohedral metallofullerenes will be produced for a wide range of helium to nitrogen ratios, but yield of the metallofullerenes may tend to decrease as the amount of nitrogen approaches the amount of helium.

In order to form the trimetallic nitride endohedral metallofullerene, a source of nitrogen must be introduced into the reaction chamber. The source of nitrogen is preferably a nitrogen containing gas, but may include other nitrogen sources including but not limited to carbon nitrides and metal nitrides where the metal to be encapsulated is in nitride form.

A potential is applied across the electrodes resulting in an arc discharge. The arc discharge consumes the graphite rod and generates a wide range of carbon products generally referred to as soot. Within the soot is a wide range of fullerenes including the trimetallic nitride endohedral metallofullerenes. Isolation of the trimetallic nitride endohedral metallofullerenes can include using carbon disulfide or toluene to extract the soluble fullerenes from the soot. All members of the trimetallic nitride endohedral metallofullerenes, Er$_{3-n}$Sc$_n$N@C$_{80}$, Ho$_{3-n}$Sc$_n$N@C$_{80}$, Y$_{3-n}$Sc$_n$N@C$_{80}$, Gd$_{3-n}$Sc$_n$N@C$_{80}$ and La$_{3-n}$Sc$_n$N@C$_{80}$ where n=0–3, are extractable in carbon disulfide except Yb$_{3-n}$Sc$_n$N@C$_{80}$ and Tm$_{3-n}$Sc$_n$N@C$_{80}$ (n=0–3).

The carbon disulfide extract is preferably filtered over a plug of glass wool to remove insoluble material. The extract can then be preferably subjected to a multi-stage chromatographic separation. The soluble extract can be separated using an initial chromatographic separation stage that incorporates a pentabromobenzyl column using carbon disulfide as the mobile phase. One such column is available from Phenomenex Co., Torrance, Calif. In the second and third stages, a selective semi-preparative Trident-Tri-DNP (di-nitorphenyl) column (Regis Chemical, Morton Grove, Ill.) may be utilized for isolation of $A_{3-n}X_nN@C_{80}$ with toluene as the solvent. A final separation stage utilizing the pentabromobenzyl column described above using $CS_2$ as the mobile phase may be used. The mobile phase elution rate is preferably about 2 ml/min. In this manner, pure $A_{3-n}X_nN@C_{80}$ samples may be isolated. Based on the foregoing, with modifications that will be apparent to one skilled in the art, this method can be used generally to obtain materials in the family of $A_{3-n}X_nN@C_m$, preferably where m is about 68, 78, or 80.

Following pegylation and hydroxylation, an endohedral metallofullerene can have the formula: $A_{3-n}X_nN@C_m(-R(-[-O-CH_2CH_2-]_k-Q)_j)_i(-OH)_h$; where A and X are metal atoms, n=0–3; m is an even number between about 60 and about 200; 1<h<m−2; i≧1; j=1 or 2; and k>1. The group $(-R(-[-O-CH_2CH_2-]_k-Q)_j)$ represents PEG linked to the fullerene by R which can be derivatized by a group Q. The combination of pegylation and hydroxylation that has been described provides greater water solubility and reduced aggregation than hydroxylation of alone. It should be recognized that the examples shown are not limiting. For example, one skilled in the art will appreciate that compounds other than ethyl malonyl chloride and malonyl dichloride can be used to link a PEG moiety with the fullerene cage.

Thus, R in the above formula can be a malonyl group in a di-PEG or an ethyl-malonyl group for a mono-PEG example or any suitable linking moiety. Further, PEG derivatives other than the methyl ether form illustrated in the above examples can be utilized in combination with hydroxylation to increase water solubility while minimizing aggregation. Thus Q could be O-methyl, a protecting group, or a functional group. For example, a segment of PEG can be used as a linker to attach a functional moiety to trimetallic nitride endohedral metallofullerenes in addition to enhancing water solubility of the molecular complex and reducing aggregation. Examples of functional moieties include an antigen, an antibody fragment, a membrane anchoring sequence, a polynucleotide, a receptor ligand, biotin, and the like. The functional moiety I can be chosen to correspond to a feature of the desired target of the pegylated and hydroxylated trimetallic nitride endohedral metallofullerenes. The PEG may be derivatized before or modified after pegylation and hydroxylation of the fullerene. The specific choice of PEG molecular weight, and whether the PEG is derivatized with a methyl group or another functional moiety, will depend on the application.

Figure 3:
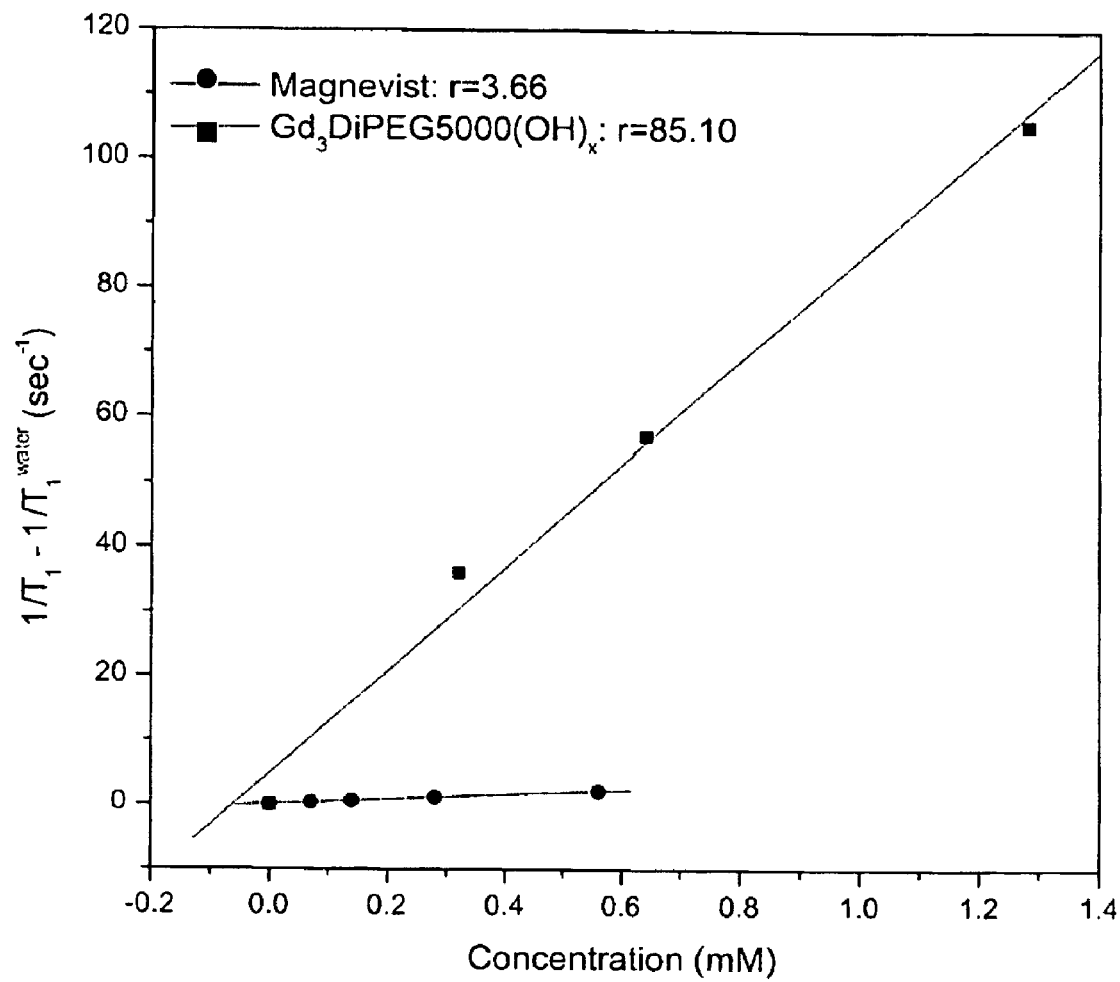
FIG. 3 shows the change in relaxation rate (1/T1) of water as a function of concentration for $Gd_3N@C_{80}$(malonyl diPEG5000)(OH)x compared to the commercial MRI contrast agent Magnevist@. PEG5000 is PEG methyl ether having a molecular weight of about 5000.

The choice of fullerene cage size and encapsulated metal are also open to the skilled practitioner to choose according to the desired application. For example, a preferred utility for pegylated and hydroxylated trimetallic endohedral metallofullerenes is as MRI contrast agents. In MRI, a signal is received from atoms in a magnetic field in response to a pulse of radio waves. The most common atoms used for MRI are the hydrogens, particularly the hydrogens of water, which is found everywhere in a body. Contrast between water in fluid compartments such as vessels and solid organs is observed because signal from atoms in different environments decays more or less quickly (relaxes) after a radio pulse. Trivalent metals, for example, can provide effective changes in signal relaxation in an MRI contrast agent application. Accordingly, a method of using pegylated and hydroxylated trimetallic endohedral metallofullerenes can comprise introducing a composition comprising pegylated and hydroxylated trimetallic endohedral metallofullerenes into a body prior to or during an MRI procedure. The pegylated and hydroxylated trimetallic endohedral metallofullerenes can provide substantially greater relaxivity than presently used contrast reagents as shown in FIG. 3. As alternative examples, metal atoms such as radioactive atoms can be encapsulated for use in treatment methods or as tracers that can be detected by radiation or x-ray.

While the invention has been described in detail with reference to preferred embodiments thereof, it will be apparent to one skilled in the art that various changes can be made, and equivalents employed, without departing from the scope of the invention.

The invention claimed is:

1. An endohedral metallofullerene of the formula: $A_{3-n}X_nN@C_m(-R(-[-O-CH_2CH_2-]_k-Q)_j)_i(-OH)_h$; where A and X are metal atoms, n=0–3; m is an even number between about 60 and about 200; 1<h<m−2; i≧1; j=1 or 2; and k>1 wherein R is a malonyl group or an ethyl-malonyl group and Q is a methoxy group or a functional group selected from among an antigen, an antibody fragment, a membrane anchoring sequence, a polynucleotide, a receptor ligand, and biotin.

2. The endohedral metallofullerene of claim 1, wherein j=1 and R is an ethyl malonyl group.

3. The endohedral metallofullerene of claim 1, wherein Q is a methoxy group.

4. The endohedral metallofullerene of claim 1, wherein j=2 and R is a malonyl group.

5. The endohedral metallofullerene of claim 1, wherein k is about 7.

6. The endohedral metallofullerene of claim 1, wherein k is about 1.

7. The endohedral metallofullerene of claim 1, wherein k is about 16 or greater.

8. The endohedral metallofullerene of claim 1, wherein k is about 40 or greater.

9. The endohedral metallofullerene of claim 1, wherein, A and/or X are rare earth element and/or a group IIIB element.

10. The endohedral metallofullerene of claim 1, wherein A and/or X are chosen from among the group consisting of Scandium, Yttrium, Lanthanum, Gadolinium, Holmium, Erbium, Thulium, and Ytterbium.

* * * * *